US00PP19014P2

(12) United States Plant Patent
Peek

(10) Patent No.: US PP19,014 P2
(45) Date of Patent: Jul. 15, 2008

(54) ***PAPAVER* PLANT NAMED 'CASINO'**

(50) Latin Name: *Papaver orientale*
Varietal Denomination: Casino

(75) Inventor: Eleonore Peek, Oudelande (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 11/705,866

(22) Filed: Feb. 14, 2007

(51) Int. Cl.
*A01H 5/00* (2006.01)

(52) U.S. Cl. ..... Plt./464

(58) Field of Classification Search ..... Plt./464, Plt./263

See application file for complete search history.

*Primary Examiner*—Kent Bell
*Assistant Examiner*—June Hwu
(74) *Attorney, Agent, or Firm*—C. A. Whealy

(57) ABSTRACT

A new, and distinct cultivar of *Papaver* plant named 'Casino' characterized by its upright plant habit; moderately vigorous growth habit; and large flowers with white and black-colored petals.

2 Drawing Sheets

Botanical designation: *Papaver orientale.*
Cultivar denomination: 'Casino'.

BACKGROUND OF THE INVENTION

The present invention relates to a new and distinct cultivar of *Papaver,* botanically known as *Papaver orientale* and hereinafter referred to by the name 'Casino'.

The new *Papaver* originated from a cross-pollination of two unnamed selections of *Papaver orientale,* not patented. The new *Papaver* was discovered and selected by the Inventor as a single flowering plant from within the progeny of the stated cross-pollination grown in a controlled environment in Oudelande, The Netherlands in May, 2003.

Asexual reproduction of the new cultivar by divisions since 2004 in Oudelande, The Netherlands has shown that the unique features of this new *Papaver* are stable and reproduced true to type in successive generations.

SUMMARY OF THE INVENTION

Plants of the cultivar Casino have not been observed under all possible environmental conditions. The phenotype may vary somewhat with variations in environment such as temperature and light intensity without, however, any variance in genotype.

The following traits have been repeatedly observed and are determined to be the unique characteristics of 'Casino'. These characteristics in combination distinguish 'Casino' as a new and distinct cultivar of *Papaver:*

1. Upright plant habit.
2. Moderately vigorous growth habit.
3. Large flowers with white and black-colored petals.

Plants of the cultivar Casino differ from plants of the parent selections primarily in flower color and plant height.

Plants of the new *Papaver* can be compared to plants of the *Papaver orientalis* cultivar Perry's White, not patented. In side-by-side comparisons conducted in Oudelande, The Netherlands, plants of the new *Papaver* differed from plants of the cultivar Perry's White in the following characteristics:

1. Plants of the new *Papaver* were shorter than plants of the cultivar Perry's White.
2. Plants of the new *Papaver* had larger flowers with more petals than plants of the cultivar Perry's White.
3. Flowers of plants of the new *Papaver* were white and black in color whereas flowers of plants of the cultivar Perry's White were creamy white and black in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Papaver.*

The photograph on the first sheet is a side perspective view of typical plants of 'Casino' grown in an outdoor nursery.

The photograph on the second sheet is a close-up view of a typical flower of 'Casino'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the summer in an outdoor nursery in Boskoop, The Netherlands. During the production of the plants, day temperatures ranged from 14° C. to 32° C. and night temperatures ranged from 7° C. to 16° C. Plants used for the photographs and the description were about two years old.

Botanical classification: *Papaver orientale* cultivar Casino.
Parentage:

*Female parent.*—Unnamed selection of *Papaver orientale,* not patented.

*Male parent.*—Unnamed selection of *Papaver orientale,* not patented.

Propagation:

*Type.*—By divisions.

*Time to initiate roots.*—About three weeks at 20° C.

*Time to produce a rooted young plant.*—About six weeks at 20° C.

*Root description.*—Thick, fleshy; brown in color.

*Rooting habit.*—Freely branching.

Plant description:

*Form.*—Herbaceous perennial flowering plant; mostly upright. Basally branching, rosette; flowering stems arise from the base. Moderately vigorous growth habit.

*Plant height, including flowers.*—About 67 cm.

*Plant height, excluding flowers.*—About 57 cm.

*Plant width.*—About 62 cm.

*Branch description.*—Arrangement: Basal branching; about seven basal branches develop per plant. Length: About 57 cm. Diameter: About 7 mm. Internode length: About 10.3 cm. Strength: Strong. Aspect: Upright. Texture: Pubescent; rough. Color: 144A.

Foliage description:

*Arrangement.*—Alternate, simple.

*Length.*—About 28.9 cm.

*Width.*—About 8.2 cm.

*Shape.*—Roughly lanceolate; mostly pinnatisect, towards the apex, pinnatifid.

*Apex.*—Acute.

*Base.*—Cuneate.

*Margin.*—Serrate.

*Texture, upper and lower surfaces.*—Pubescent; rough.

*Venation pattern.*—Pinnate.

*Color.*—Developing foliage, upper surface: Between 137A and 143A. Developing foliage, lower surface: 138A. Fully expanded foliage, upper surface: Between 137A and 143A; venation, 138C to 138D. Fully expanded foliage, lower surface: 137D; venation, 143B.

*Petiole length.*—About 18.7 cm.

*Petiole diameter.*—About 7 mm.

*Petiole color, upper and lower surfaces.*—144B.

Flower description:

*Flower arrangement and appearance.*—Large semi-double rotate flowers; flowers terminal and face mostly upright; about seven flowers per plant at one time.

*Natural flowering season.*—Continuous flowering from mid-June to mid-July in The Netherlands.

*Flower longevity on the plant.*—About three days; flowers not persistent.

*Fragrance.*—None detected.

*Flower buds.*—Length: About 4 cm. Diameter: About 2.5 cm. Shape: Elliptic to ovate. Texture: Densely pubescent. Color: 146B to 146C.

*Flower diameter.*—About 12.2 cm.

*Flower depth* (*height*).—About 8.3 cm.

*Petals.*—Arrangement: About six in two whorls. Length: About 8 cm. Width: About 8.1 cm. Shape: Broadly obovate. Apex: Shallow and irregularly praemorse; slightly ruffled in appearance. Margin: Irregular, deeply incised; undulate; ruffled in appearance. Texture, upper and lower surfaces: Smooth, glabrous. Color: When opening and fully opened, upper surface: Close to 155D; towards the base, spot, between N186C and 202A. When opening and fully opened, lower surface: Close to 155D; towards the base, spot, between N186C and 202A.

*Sepals.*—Arrangement: About four in a single whorl. Length: About 3.4 cm. Width: About 1.2 cm. Shape: Oblong, narrow. Apex: Acute. Margin: Serrate. Texture, upper and lower surfaces: Densely pubescent. Color, upper surface: Between 137A and 143A. Color, lower surface: 137D.

*Peduncles.*—Length: About 57.9 cm. Diameter: About 7 mm. Strength: Strong. Texture: Pubescent; rough. Color: 144A to 144B.

*Reproductive organs.*—Stamens: Quantity per flower: About 250. Filament length: About 1.5 cm. Filament color: 187A. Anther shape: Narrowly oblong. Anther length: About 3 mm. Anther color: N187A. Pollen amount: Scarce. Pollen color: 197C. Pistils: Quantity per flower: About eleven. Pistil length: About 8 mm. Stigma shape: Narrowly oblong. Stigma color: 186B. Ovary color: 143B.

*Fruits.*—Type: Capsule. Quantity per flower: One. Length: About 3.8 cm. Diameter: About 2.8 cm. Color: 137A.

*Seeds.*—Quantity per fruit: About 900. Length: About 1 mm. Diameter: About 1 mm. Color: 202A to 202B.

Disease/pest resistance: Plants of the new *Papaver* have not been noted to be resistant to pathogens and pests common to *Papaver.*

Garden performance: Plants of the new *Papaver* have exhibited good tolerance to rain, wind, and temperatures ranging from about −20° C. to about 40° C.

It is claimed:

1. A new and distinct *Papaver* plant named 'Casino' as illustrated and described.

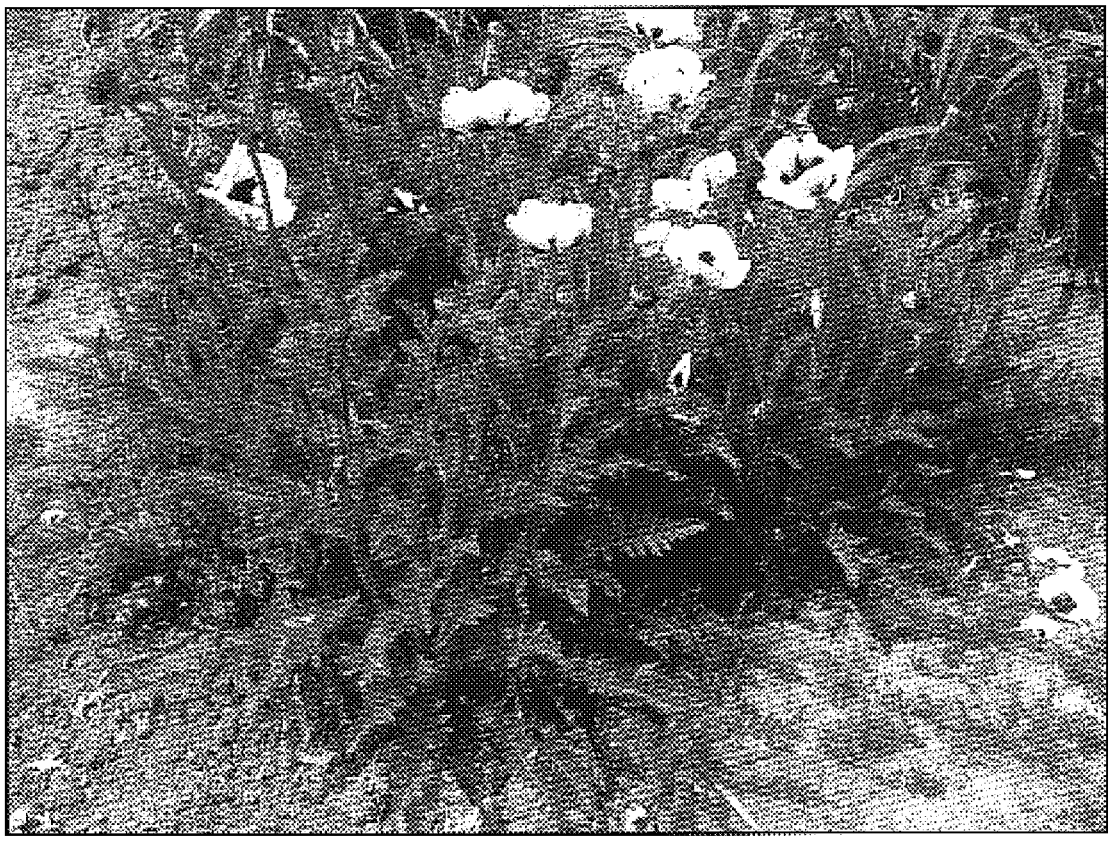

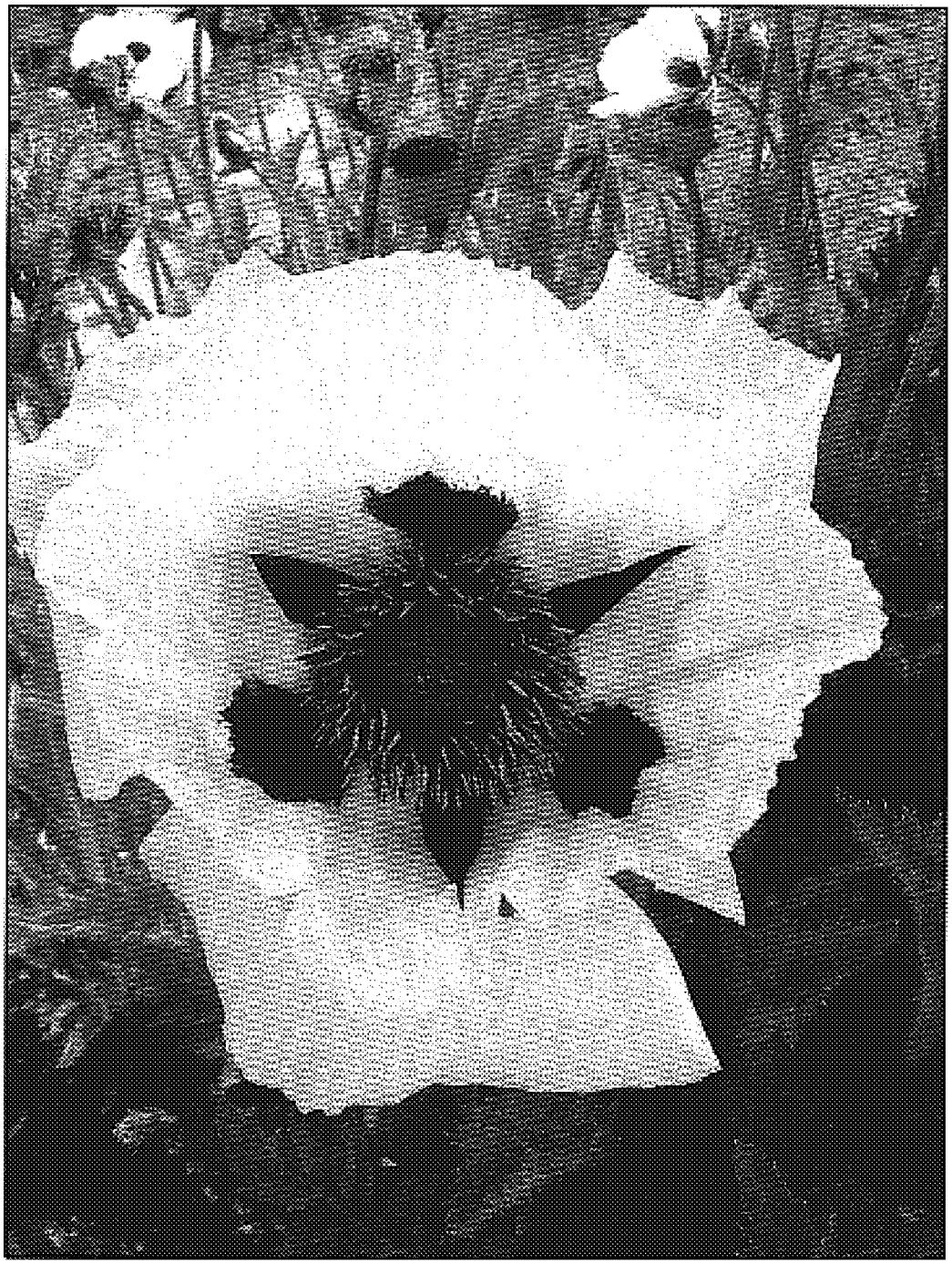

* * * * *